(12) United States Patent
Hünig et al.

(10) Patent No.: US 12,235,255 B2
(45) Date of Patent: Feb. 25, 2025

(54) METHOD OF DETERMINING CHEMICAL OXYGEN DEMAND (COD) FOR HIGH CHLORIDE SAMPLES

(71) Applicant: HACH LANGE GMBH, Berlin (DE)

(72) Inventors: Isabel Hünig, Dusseldorf (DE); Carsten Schulz, Dormagen (DE); Helga Guthmann, Grevenbroich (DE); Ralf Kloos, Schwerte (DE)

(73) Assignee: HACH LANGE GMBH, Berlin (DE)

( * ) Notice: Subject to any disclaimer, the term of this patent is extended or adjusted under 35 U.S.C. 154(b) by 752 days.

(21) Appl. No.: 17/253,503

(22) PCT Filed: Jun. 19, 2019

(86) PCT No.: PCT/EP2019/066212
§ 371 (c)(1),
(2) Date: Dec. 17, 2020

(87) PCT Pub. No.: WO2020/007611
PCT Pub. Date: Jan. 9, 2020

(65) Prior Publication Data
US 2021/0270794 A1  Sep. 2, 2021

(30) Foreign Application Priority Data
Jul. 4, 2018 (EP) .................................. 18181661

(51) Int. Cl.
*G01N 33/18* (2006.01)
*G01N 21/31* (2006.01)
(52) U.S. Cl.
CPC ......... *G01N 33/1806* (2013.01); *G01N 21/31* (2013.01)

(58) Field of Classification Search
CPC ........................... G01N 33/1806; G01N 21/31
See application file for complete search history.

(56) References Cited

U.S. PATENT DOCUMENTS

| | | | |
|---|---|---|---|
| 3,540,845 A | 11/1970 | Overbeck et al. | |
| 2014/0322814 A1* | 10/2014 | Olt ....................... | G01N 21/314 436/62 |

OTHER PUBLICATIONS

James M. Cripps, A COD method suitable for the analysis of highly saline waters, Oct. 1964, Journal (Water Pollution Control. Federation), vol. 36, pp. 1240-1246 (Year: 1964).*

(Continued)

*Primary Examiner* — Jill A Warden
*Assistant Examiner* — Alex Ramirez
(74) *Attorney, Agent, or Firm* — Ference & Associates LLC

(57) ABSTRACT

The present invention provides a method of determining chemical oxygen demand (COD) for a sample with a high concentration of chloride. The method includes obtaining the sample, determining a concentration of chloride in the sample to obtain a known concentration of chloride in the sample, dosing an amount of the sample, an acid and an oxidizing agent into a container to obtain an analyte, heating the container containing the analyte, photometrically determining a preliminary chemical oxygen demand (COD) of the analyte in an analytic device, and correcting for the high concentration of chloride using a chloride correction to obtain the chemical oxygen demand (COD).

8 Claims, 4 Drawing Sheets

(56) References Cited

OTHER PUBLICATIONS

LCK Cuvette Tests: The professional solution for staying compliant, Mar. 2016, "Benefits of the LCK cuvette tests", p. 3 retrieved from: https://mena.hach.com/cod-cuvette-test-150-1000-mg-l-o-25-tests/product-downloads?id=26899505512 (Year: 2016).*

Burns and Craig Marshall E R: Correction for Chloride Interference in the Chemical Oxygen Demand Test, Journal—Water Pollution Control Federation, the Federation, Washington, DC US, vol. 37, No. 12, Dec. 1965 (Dec. 1965), pp. 1716-1721.

International Searching Authority, Notification of Transmittal of the International Search Report and the Written Opinion of the International Searching Authority, or the Declaration, date of mailing Jul. 24, 2019, pp. 12.

James M Cripps and David Jenkins: "A COD Method Suitable for the Analysis of Highly Saline Waters", Journal—Water Pollution Control Federation, the Federation, Washington, DC, US vol. 36, No. 10, Oct. 1964 (Oct. 1964), pp. 1240-1246.

* cited by examiner

| | | |
|---|---|---|
| 1. Shake vigorously to bring the sediment fully into suspension. | 2. Immediately pipette 1.8 ml of sample: | 3. Immediately close the cuvette and shake. |
| 4. Thoroughly clean the outside of the cuvette. | 5. Heat in the thermostat. COD classic: for 2 hours at 148 °C (298.4 °F). HT 200 S: in the standard program HT for 15 minutes. | 6. Remove the hot cuvette. COD classic: Carefully invert twice. HT 200 S: After the lock opens, carefully invert. |
| 7. Allow to cool to room temperature. COD classic: in a cooling rack. HT 200 S: in the thermostat. | 8. Thoroughly clean the outside of the cuvette and evaluate. The sediment must be completely settled before evaluation is carried out. | 9. Insert the cuvette into cell holder. Select evaluation method depending on thermostat used. |

Fig.3

METHOD OF DETERMINING CHEMICAL OXYGEN DEMAND (COD) FOR HIGH CHLORIDE SAMPLES

The present invention relates to a method of determining chemical oxygen demand (COD) for high chloride samples.

Chemical oxygen demand (COD) is an indicative measure of the amount of oxygen that can be consumed by reactions in a measured solution. It is commonly expressed in mass of oxygen consumed over volume of solution, which in SI units is milligrams per liter (mg/L). A COD test can be used to quantify the amount of organics in water. The most common application of COD is in quantifying the amount of oxidizable pollutants found in surface water, such as lakes and rivers, or wastewater. COD is useful in terms of water quality by providing a metric to determine the effect an effluent will have on the receiving body, much like biochemical oxygen demand (BOD).

The basis for the COD test is that nearly all organic compounds can be fully oxidized to carbon dioxide with a strong oxidizing agent under acidic conditions. One such strong oxidizing agent under acidic conditions is potassium dichromate ($K_2Cr_2O_7$). Acidity is thereby usually achieved via the addition of sulfuric acid ($H_2SO_4$). The reaction of potassium dichromate with organic compounds is given by:

$$C_nH_aO_bN_c + dCr_2O_7^{2-} + (8d+c)H^+ \rightarrow$$
$$nCO_2 + \frac{a+8d-3c}{2}H_2O + cNH_4^+ + 2dCr^{3+}$$

where d=2n/3+a/6−b/3−c/2. A 0.25 N solution of potassium dichromate is normally used for COD determination, although a lower concentration of potassium dichromate can also be used for samples with COD below 50 mg/L.

In the process of oxidizing the organic substances found in the water sample, potassium dichromate is reduced (since in all redox reactions, one reagent is oxidized and the other is reduced), thereby forming $Cr^{3+}$. The decrease of $Cr_2O_7^{2-}$ or the amount of $Cr^{3+}$ formed is determined after the oxidization is complete and is used as an indirect measure of the organic contents of the water sample.

An excess amount of potassium dichromate (or some other oxidizing agent) must be present for all organic matter to be completely oxidized. Once oxidation is complete, the amount of excess potassium dichromate, or the amount of $Cr^{3+}$ formed, can be accurately determined either by titration with ferrous ammonium sulfate (FAS or $(NH_4)_2Fe(SO_4)_2 \cdot 6H_2O$) or by photometry. If photometry is used, the absorption at, for example, 605 nm, can be used to measure the $Cr^{3+}$ formed during oxidation, or the decrease of absorption, for example, at 348 nm and/or at 448 nm, can be used to determine the consumption of $Cr_2O_7^{2-}$.

Some samples of water contain high levels of oxidizable inorganic materials which may interfere with the determination of COD. Chloride ($Cl^-$) is often the most serious source of interference because of its high concentration in some wastewaters. Other samples, such as seawater and brackish water, also exhibit naturally high chloride concentrations. The chloride reaction with potassium dichromate follows the equation:

$$6Cl^- + Cr_2O_7^{2-} + 14H^+ \rightarrow 3Cl_2 + 2Cr^{3+} + 7H_2O$$

Various methods have previously been described to determine chemical oxygen demand (COD) for samples containing chloride.

DIN 38409-41 describes the determination of chemical oxygen demand (COD) by means of titration. This standard describes under method 41-1 a titrimetric method for samples having a chloride content up to 1,000 mg/L. Method 41-2 of DIN 38409-41 describes a method to expel the chloride content of samples having a chloride content above 1,000 mg/L. After the chloride is expelled, the chemical oxygen demand (COD) can be determined by means of oxidation with chromic acid and titration as described under 41-1.

DIN ISO 15705 describes the photometric determination of the chemical oxygen demand (COD) via a cell test. This determination is, however, restricted to samples having a maximum chloride content of 1,000 mg/L.

The International Organization for Standardization describes a standard method for measuring chemical oxygen demand in ISO 6060 (1989). The ISO 6060 method is applicable to water with a value between 30 mg/L and 700 mg/L. The ISO 6060 method is only accurate, however, if the chloride concentration does not exceed 1,000 mg/L. If the chloride value exceeds 1,000 mg/L, the water sample must be diluted. The greatest accuracy for the ISO 6060 method is achieved when the COD value of the sample is in the range of 300 mg/L to 600 mg/L.

Another previously described procedure for determining COD involves the dichromate reflux method which utilizes acid concentrations and heating times which will oxidize roughly 85-95% of the organic matter present, but which will also oxidize essentially 100% of the chloride ions. In this procedure, interference by chloride ions, at moderate concentrations, is largely prevented through the addition of mercury (II) sulfate to form unionized mercuric chloride. The complexing method uses a weight ratio of $HgSO_4$:Cl equal to 10:1 to yield reproducible results at chloride concentrations of up to 5,000 mg/L. Problems due to chloride interference still arise, however, in wastes of low to moderate COD with chloride concentrations approaching that of seawater.

Baumann describes a method which quantifies and accounts for chloride concentrations in highly saline wastes which were oxidized using the dichromate reflux method. Baumann thereby uses a chloride-collection apparatus to liberate and collect chloride in an acid potassium iodide solution, followed by back-titrating vs. a standard sodium thiosulfate solution to then arrive at a chloride correction. Frank J. Baumann, Dichromate Reflux Chemical Oxygen Demand, A Proposed Method for Chloride Correction in Highly Saline Wastes, Analytical Chemistry, Volume 46, No. 9, pp. 1336-1338 (August 1974).

Another previously described method to eliminate chloride interference is to add mercury (II) sulfate ($HgSO_4$) prior to the addition of other reagents to mask the presence of chloride. The mercury (II) sulfate thereby complexes the chloride, with silver sulfate being used as a catalyst. E. R. Burns and Craig Marshall, Correction for Chloride Interference in the Chemical Oxygen Demand Test, J Water Pollution Control Fed., Vol. 37, No. 12, pp. 1716-1721 (December 1965).

The addition of mercury (II) sulfate can only eliminate chloride interference up to a chloride concentration of about 1,500 mg/L. A sample will generally need to be diluted if the chloride concentration exceeds 1,500 mg/L. One such test is currently sold under the NANOCOLOR® brand and uses 3.7 to 15% of mercury (II) sulphate when chloride content is between 1,000 and 7,000 mg/L. This test requires a preliminary test to determine the chloride concentration, from which a required dilution can be calculated and directly prepared.

The addition of mercury (II) sulfate has both health and environmental issues. Inhalation of mercury (II) sulfate can result in acute poisoning, causing tightness in the chest, difficulties breathing, coughing and pain. Exposure of mercury (II) sulfate to the eyes can cause ulceration of conjunctiva and cornea. Exposure of the skin to mercury sulfate may cause sensitization dermatitis. Ingestion of mercury sulfate will cause necrosis, pain, vomiting, and severe purging and can even result in death within a few hours due to peripheral vascular collapse. The NANOCOLOR® brand itself warns users to immediately call the poison center if the test contents are swallowed. Mercury (II) sulfate is toxic, its use results in toxic waste, and is therefore also not preferred for environmental reasons. Tests which rely only on the use of mercury (II) sulfate also struggle to achieve reproducible results.

U.S. Pat. No. 9,091,674 B2 describes a method of determining the chemical oxygen demand (COD) of chloride-containing samples photometrically without using mercury (II) sulfate. The chloride-containing sample is thereby first treated with sulfuric acid to expel the chloride ions. The photometric determination of the chemical oxygen demand (COD) is subsequently carried out using a reagent solution. While U.S. Pat. No. 9,091,674 B2 describes that the addition of mercury (II) sulfate to the reagent solution is generally unnecessary, various preferred embodiments still include mercury (II) sulfate.

The object of the present invention is to provide a method to accurately determine chemical oxygen demand (COD) for high chloride samples which reduces or entirely avoids the use of mercury (II) sulfate, which is simple to use, and which can be used with existing analytical devices.

The present invention provides a method of determining chemical oxygen demand (COD) for a sample comprising a high concentration of chloride.

The method includes obtaining the sample, determining a concentration of chloride in the sample to obtain a known concentration of chloride in the sample, dosing an amount of the sample, an acid and an oxidizing agent into a container to obtain an analyte, heating the container containing the analyte, photometrically determining a preliminary chemical oxygen demand (COD) of the analyte in an analytic device, and correcting for the high concentration of chloride using a chloride correction to obtain the true chemical oxygen demand (COD).

The step of determining a concentration of chloride in the sample needn't be provided before the photometric determination of the preliminary chemical oxygen demand (COD) but can also be provided after the photometric determination but before the correction step.

The step of dosing of an acid and an oxidizing agent into a container can also be realized pre-dosed or pre-fabricated. The user receives the container with the correctly pre-dosed acid and oxidizing agent so that the user has only to dose the suitable amount of the sample into the container.

The present invention is described in greater detail below on the basis of embodiments and of the drawings in which:

FIG. 3 shows a sample workflow for a method of the present invention;

Figure 1:
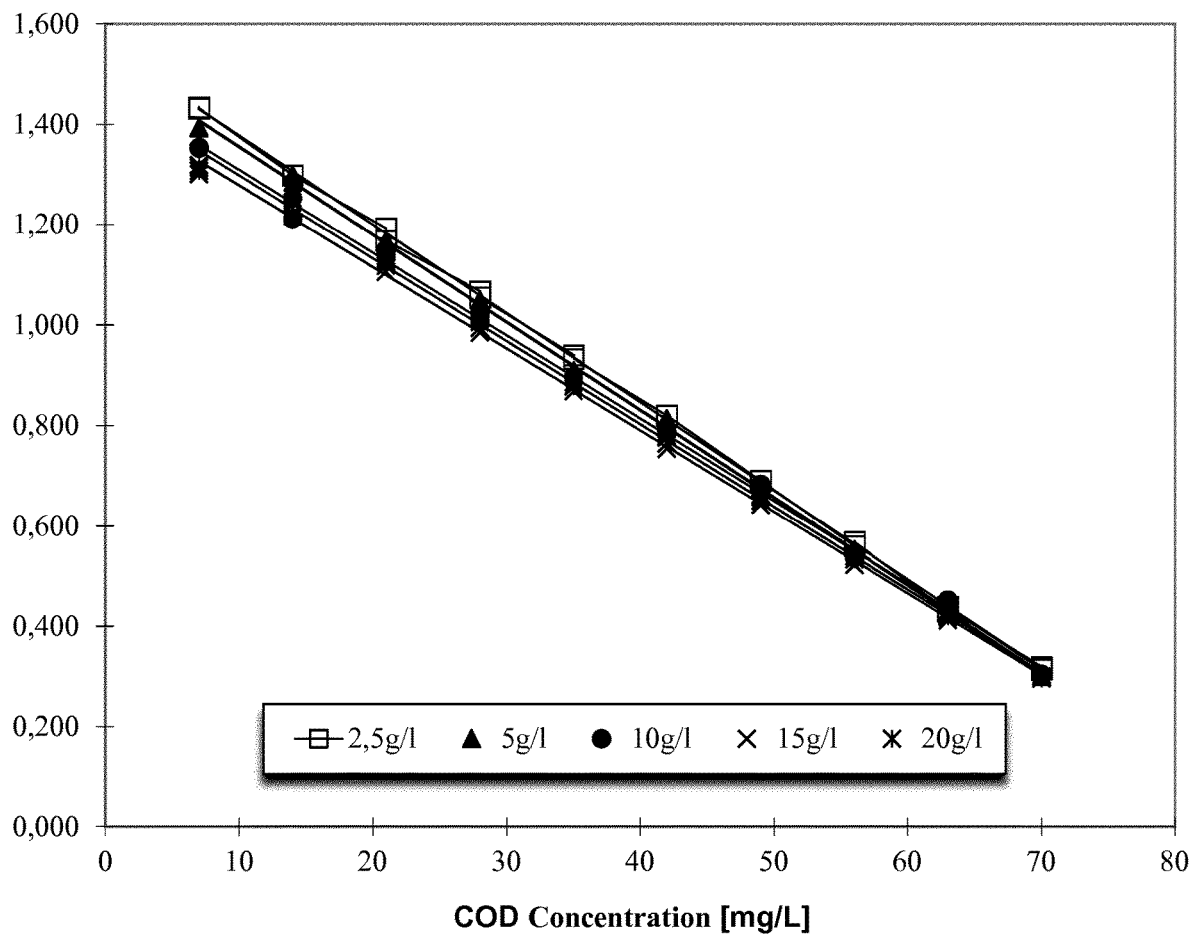
FIG. 1 shows a suite of calibration curves for different chloride contents which can be used as the basis for determining the chloride correction of the present invention.

A "high chloride concentration" as used in the present invention is understood to be a chloride concentration of ≥1,500 mg/L to 20,000 mg/L, preferably ≥2,000 mg/L to 20,000 mg/L. The method of the present invention can also be used for chloride concentrations which exceed 20,000 mg/L, however, the sample will then need to be diluted, preferably with deionized water or with another diluent whose chloride concentration is known and/or whose chemical oxygen demand (COD) has previously been determined. The container containing the analyte is preferably cooled prior to photometrically determining the preliminary chemical oxygen demand (COD) of the analyte.

The acid of the present invention can be any a molecule or ion capable of donating a hydron (proton or hydrogen ion $H^+$) or which is capable of forming a covalent bond with an electron pair (i.e., a Lewis acid) without interfering with the determination of chemical oxygen demand (COD). Sulfuric acid ($H_2SO_4$) is preferably used as the acid in the present invention. The oxidizing agent can be any strong oxidizing agent which fully oxidizes organic compounds to carbon dioxide under acidic conditions. The oxidizing agent is preferably a chromate salt containing the chromate anion, $CrO^{2-}$, or dichromate salts containing the dichromate anion, $Cr_2O_2^{-7}$. Potassium dichromate ($K_2Cr_2O_7$) is preferably used as the oxidizing agent in the present invention. The sample is preferably heated to a temperature from 120 to 180° C., preferably from 140 to 170° C., very preferably to about or exactly to 148° C. or to about or exactly to 170° C., for 15 to 150 min. The analytic device is preferably a photometer. Examples of preferred photometers include the DR6000™ UV VIS Spectrophotometer with RFID Technology and/or the DR3900™ Benchtop Spectrophotometer with RFID Technology, each from Hach.

The container used in the present invention is preferably a vial or a cuvette. If a cuvette is used, it is preferable if the cuvette and/or cuvette batch has previously been calibrated in order to additionally minimize any potential sources of measurement error. Cuvettes such as the LCK 1414 from Hach can preferably be used. The LCK 1414 cuvettes from Hach are provided with pre-dosed reagents so that only the correct amount of sample, or sample diluted with, for example, water, needs to be dosed therein. A precise and reliable measurement is thereby provided. The LCK 1414 cuvettes from Hach are additionally coded with a barcode so that a photometer can automatically recognize the cuvette and adjust any measurement result via a calibration value which has previously been determined for the cuvette/batch of cuvettes. This also provides for a more precise measurement result, for example, a more precise determination of chemical oxygen demand (COD).

The container can preferably include mercury (II) sulfate ($HgSO_4$). The dosing of the container with the acid, the oxidizing agent and/or the mercury (II) sulfate preferably occurs prior to the dosing of the amount of the sample into the container. The container is preferably provided with the acid, the oxidizing agent and/or the mercury (II) sulfate as pre-dosed reagents in the container.

An important aspect of the present invention is the use of the so-called "chloride correction". The chloride correction is preferably individually determined for and saved in a photometer, for example, as a previously-determined range for the photometer which then only needs to be applied (for example via reading the result, by manually inputting, and/or by manually confirming the result) by a user based on the total chemical oxygen demand (COD) measured. The chloride correction is preferably based on at least one of a table, a graph, or a mathematical formula. The present invention also provides for the use of the chloride correction in an analytic device to determine chemical oxygen demand (COD). One such graph of a chloride correction is shown in FIG. 1 and is based on the concentration of chloride as measured in the DR6000™ UV VIS Spectrophotometer with RFID Technology from Hach. A so-called "calibration curve" is thereby obtained. The calibration curves in FIG. 1 show that the measurement error based on a high chloride concentration will be higher for a low chemical oxygen demand (COD) and lower for a higher chemical oxygen demand (COD). It is believed that a reason therefor might be that large amounts of the oxidizing agent are consumed by the oxidation of organic substances at high COD concentrations. The error induced by reaction with chloride is therefore less because only a small amount of oxidizing agent remains available (mass action law). The use of multiple calibration curves to determine the chloride correction is therefore preferable in order to eliminate error.

Figure 2:
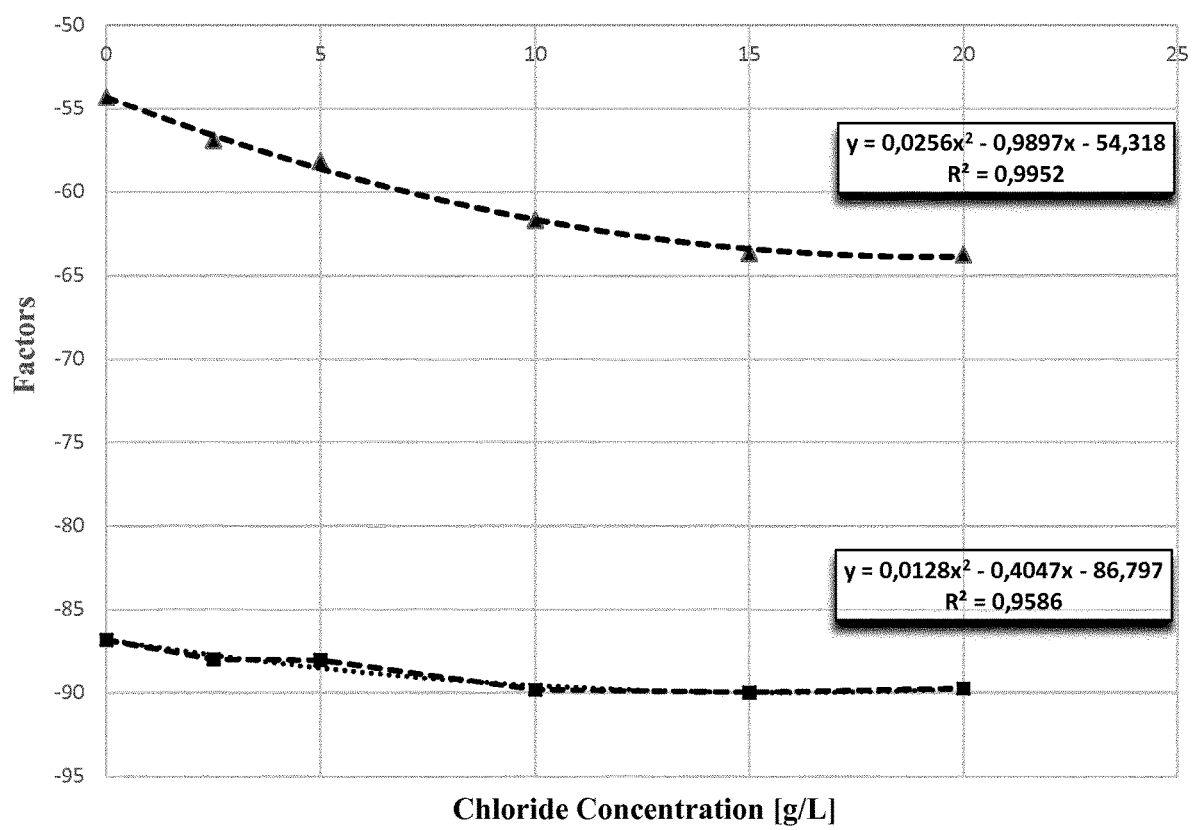
FIG. 2 shows a graph of the calibration curve factors' dependence on chloride concentration.

FIG. 2 shows the dependence of the slope (F1) and axial intercept (F2) of the calibration curve on the chloride concentration. It is possible to determine the slope (F1) and intercept (F2) of the calibration curve for any chloride concentration with the formulas derived from the graphical fits. By inserting the formulas of the graphical fits into F1 and F2, it is possible to express the COD concentration in terms of the measured absorption and chloride concentration. An exemplary formula is set forth below based on the above data where:

C(COD)=Concentration of chemical oxygen demand (COD);
F1=Slope of calibration curve;
F2=Axial intercept of the calibration curve;
Abs=Absorption (=extinction); and
C(Cl)=Chloride concentration in the sample.

The chemical oxygen demand (COD) can therefore be calculated as follows:

$$C(COD)=F1\cdot(Abs-F2) \quad [1]$$

where
$F1=[0.0256\cdot(C(Cl))^2]-[0.9897\cdot C(Cl)-54.318]$; and
$F2=[0.0128\cdot(C(Cl))^2]-[0.4047\cdot C(Cl)-86.797]$.

Inserting F1 and F2 into [1] therefore yields:

$$C(COD)=[-0.48\cdot C(Cl)-55.54]\cdot Abs+0.15\cdot C(Cl)-87.41.$$

FIG. 3 provides a sample workflow for determining chemical oxygen demand (COD) in a high chloride sample, for example, seawater. This sample workflow can be used for samples (or diluted samples) with chloride concentrations of 1.5-20 g/L.

The workflow provides that the sample is provided in a cuvette with a screw top to ensure that no additional contaminants will enter the cuvette. The cuvette containing the original sample is vigorously shaken in a first step to bring all sediment into suspension. A vortex shaker can, for example, be used to perform the shaking. Failure to bring all sediment into suspension before pipetting the sample can result in a high bias. A specific amount of the sample, for example, 1.8 ml, is then pipetted into a test cuvette containing a pre-dosed reagent, such as the sulfuric acid ($H_2SO_4$), potassium dichromate ($K_2Cr_2O_7$), and optionally the mercury (II) sulfate ($HgSO_4$). This test cuvette is then closed and shaken, cleaned, and thereafter heated, for example, for two hours at 148° C. The heated test cuvette is then removed, inverted twice, and transferred to a rack to cool. The heated test cuvette can alternatively or additionally remain in the thermostat unit it has cooled. It is thereby important for the sediment to completely settle after cooling. If this is not the case, the test cuvette should be centrifuged, for example, for 2 min. at 4,000 rpm. The cooled test cuvette is then cleaned and inserted into the measuring chamber of the photometer.

Figure 4:
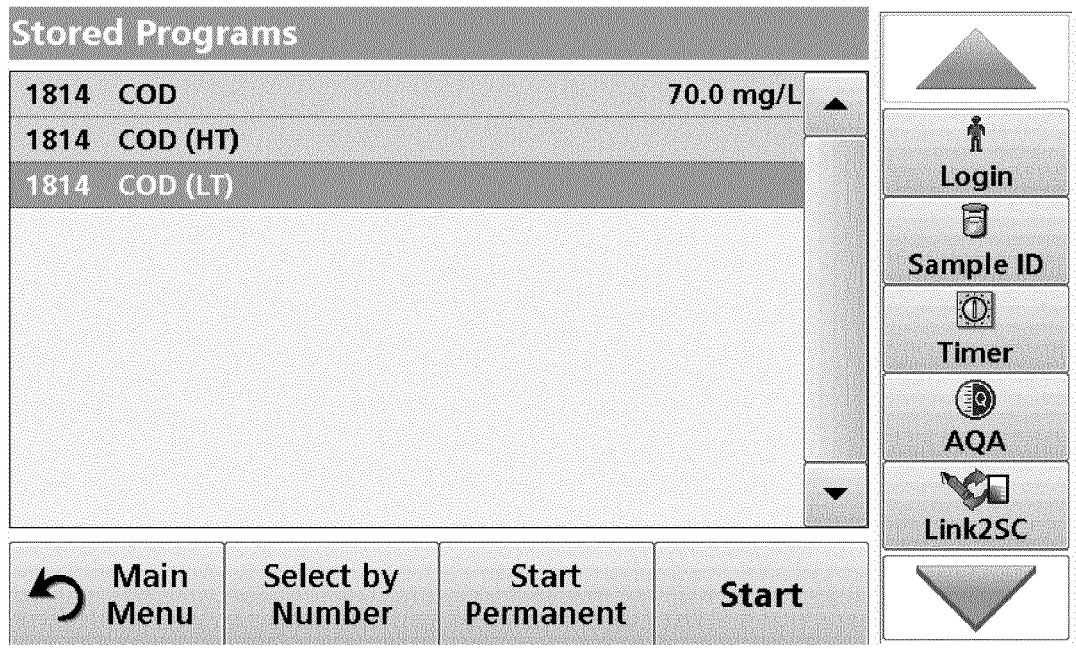
FIG. 4 shows a first screen when performing the method of the present invention on a spectrophotometer.
Figure 5:
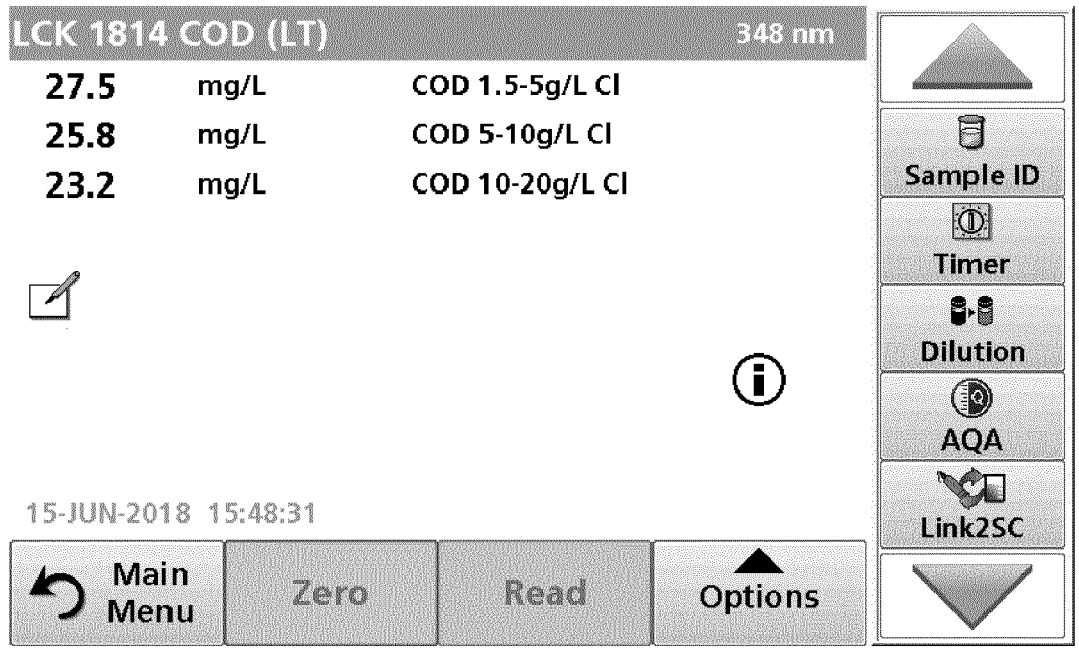
FIG. 5 shows a second screen when performing the method of the present invention on a spectrophotometer.

FIGS. 4 and 5 show the screen of a DR6000™ UV VIS Spectrophotometer as used when testing a sample having a high chloride concentration. As set forth above, the chloride concentration must first be determined. This can occur, for example, using the LCK 311 test system from Hach which can determine a chloride concentration of 1 to 1,000 mg/L or via the QUANTAB Chloride Test Strips from Hach which can determine a chloride concentration of 300 to 6,000 mg/L. Other tests to determine chloride concentration are also commercially available. A skilled person will know to dilute a sample once or more than once if the initial chloride concentration exceeds the upper limit of the chloride test used.

FIG. 4 shows a first screen showing the evaluation methods/programs which is based on the thermostat used. Listed are a first program "1814 COD (HT)" which uses a thermostat set at 170° C. for 15 min. or at 148° C. for two hours, and a second program "1814 COD (LT)" which uses a thermostat set at 148° C. for two hours. FIG. 5 shows the result upon inserting the test cuvette and choosing the 1814 COD (LT). The user obtains three readings of 27.5 mg/L COD when the chloride concentration is in the range of 1,500-5,000 mg/L, 25.8 mg/L when the chloride concentration is in the range of 5,000-10,000 mg/L, and 23.2 mg/L when the chloride concentration is in the range of 10,000-20,000 mg/L. The user then only needs to select the true chemical oxygen demand (COD) based on the known chloride concentration.

It is of course possible to provide a fully automated test where, in a first step, the chloride concentration is determined, and, in a second step, the true chemical oxygen demand (COD) is determined as corrected by an applicable chloride correction or vice versa.

The present invention is not limited to embodiments described herein; reference should be made to the appended claims.

The invention claimed is:

1. A method of determining chemical oxygen demand (COD) for a sample comprising a high concentration of chloride, the method comprising:
   obtaining the sample;
   determining a concentration of chloride in the sample to obtain a known concentration of chloride in the sample, wherein the known concentration of chloride is in a range from about 5,000 mg/L to about 20,000 mg/L;
   dosing an amount of the sample, an acid and an oxidizing agent into a cuvette to obtain an analyte, wherein the dosing comprises pre-dosed reagents of the acid and the oxidizing agent in the cuvette;
   heating the cuvette containing the analyte;
   photometrically determining a preliminary chemical oxygen demand (COD) of the analyte in the cuvette in an analytic device; and
   correcting the preliminary chemical oxygen demand (COD) using a chloride correction, to obtain the chemical oxygen demand (COD) and based upon a previously determined calibration value of the cuvette.

2. The method as recited in claim 1, further comprising:
cooling, prior to the photometrically determining, the cuvette containing the analyte.

3. The method as recited in claim 1, wherein, the acid is sulfuric acid (H2SO4);
the oxidizing agent is potassium dichromate ($K_2Cr_2O_7$);
the heating of the cuvette is to a temperature of from about 120 to about 180° C. for 15 to 150 min.; and
the analytic device is a photometer.

4. The method as recited in claim 1, wherein the cuvette further comprises mercury (II) sulfate ($HgSO_4$).

5. The method as recited in claim 4, wherein: the dosing of at least one of the acid, the oxidizing agent and the mercury (II) sulfate into the cuvette occurs prior to the dosing of the amount of the sample into the cuvette.

6. The method as recited in claim 1, further comprising:
at least one of manually inputting and manually confirming the chloride correction by a user.

7. The method as recited in claim 1, wherein the chloride correction is based on at least one of a table, a graph, or a mathematical formula.

8. A method of determining chemical oxygen demand (COD) for a sample comprising a high concentration of chloride, the method comprising:
obtaining the sample;
determining a concentration of chloride in the sample to obtain a known concentration of chloride in the sample, wherein the known concentration of chloride is ≥20,000 mg/L;
diluting the sample prior to a dosing step;
dosing an amount of the sample, an acid and an oxidizing agent into a cuvette to obtain an analyte, wherein the dosing comprises pre-dosed reagents of the acid and the oxidizing agent in the cuvette;
heating the cuvette containing the analyte;
photometrically determining a preliminary chemical oxygen demand (COD) of the analyte in the cuvette in an analytic device; and
correcting the preliminary chemical oxygen demand (COD) using a chloride correction, to obtain the chemical oxygen demand (COD) and based upon a previously determined calibration value of the cuvette.

* * * * *